United States Patent
Lai et al.

[11] Patent Number: 6,063,781
[45] Date of Patent: May 16, 2000

[54] PESTICIDAL PHENYLPYRIDAZINONE DERIVATIVES

[76] Inventors: Hoi Kiong Lai, 14 Smart Street, Guelph, Ontario, Canada, N1G 4L4; Paul Thomas McDonald, 34 Mireydam Rd., Middlebury, Conn. 06762

[21] Appl. No.: 09/251,537

[22] Filed: Feb. 17, 1999

[51] Int. Cl.[7] .......................... A01N 43/58; C07D 237/14
[52] U.S. Cl. .............................................. 514/247; 544/239
[58] Field of Search .............................. 544/239; 514/247

[56] References Cited

U.S. PATENT DOCUMENTS 4,738,961  4/1988  Jojima et al. ............................ 514/227

OTHER PUBLICATIONS

Umio et al., Cjemical abstracts, vol. 71, No. 3397 (Abstract for JP 6907337 Mar. 31, 1969).

*Primary Examiner*—Emily Bernhardt
*Attorney, Agent, or Firm*—Daniel Reitenbach

[57] ABSTRACT

Pesticidal phenylpyridazinone derivatives of the formula

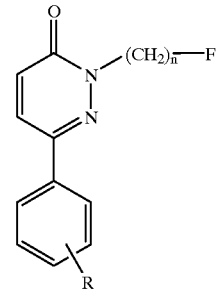

(I)

wherein n is 2, 4, 6, or 8, and R is hydrogen or one or more groups selected from halogen, nitro, $C_1$–$C_4$ haloalkyl, amino, carboxyl, carboxylate, sulfonate, and cyano, and pesticidal compositions thereof.

11 Claims, No Drawings

PESTICIDAL PHENYLPYRIDAZINONE DERIVATIVES

FIELD OF THE INVENTION

This invention relates to pesticidal phenylpyridazinone derivatives. More particularly, this invention relates to phenylpyridazinone derivatives which exhibit activity as miticides, insecticides, and/or nematicides. This invention also relates to pesticidal compositions comprising the phenylpyridazinone derivatives, and to methods of controlling acarids, insects, and nematodes using such compounds or compositions.

BACKGROUND OF THE INVENTION

The devastation caused by mites, insects, and nematodes represents a serious economic threat to commercially important food, fiber and ornamental plants. For this reason the development of new and effective miticides, insecticides, and nematicides is an ongoing scientific activity.

U. S. Pat. Nos. 4,052,395; 4,738,961; and 5,726,176 describe certain phenylpyridazinone derivatives useful as agricultural fungicides.

It is a purpose of this invention to provide novel phenylpyridazinone derivatives which are useful as pesticides.

SUMMARY OF THE INVENTION

This invention relates to a 6-phenylpyridazinone compound of the formula

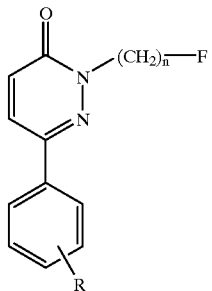

(I)

wherein n is 2, 4, 6, or 8, and R is hydrogen or one or more groups selected from halogen, nitro, $C_1$–$C_4$ haloalkyl, amino, carboxyl, carboxylate, sulfonate, and cyano.

The present invention also relates to a pesticidal composition comprising: a) a pesticidally effective amount of a compound of formula I; and b) a suitable carrier.

The present invention further relates to a method for controlling mites which comprises applying an effective amount of a miticidal compound of formula I to the locus to be protected.

The present invention additionally relates to a method for controlling insects which comprises applying an effective amount of an insecticidal compound of formula I to the locus to be protected.

The present invention additionally relates to a method for controlling nematodes which comprises applying an effective amount of an nematicidal compound of formula I to the locus to be protected.

DESCRIPTION OF THE INVENTION

This invention preferably relates to a pesticidal 6-phenylpyridazinone compound of the formula

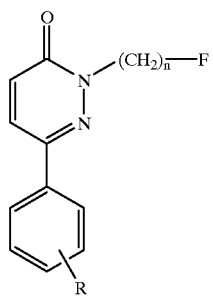

(I)

wherein R is hydrogen or one or more groups selected from halogen and $C_1$–$C_4$ haloalkyl, and n is 2 or 4. More preferably, R is one or two groups selected from halogen and trihalomethyl, and n is 2. Halogens useful as R in the compound of this invention include fluorine, chlorine, iodine, and bromine. The trihalomethyl group is preferably trifluoromethyl.

The present invention also preferably relates to a miticidal composition comprising: a) an effective amount of a miticidal compound of formula I; and b) a suitable carrier.

The present invention further relates to a insecticidal composition comprising: a) an effective amount of an insecticidal compound of formula I; and b) a suitable carrier.

The present invention additionally relates to a nematicidal composition comprising: a) an effective amount of a nematicidal compound of formula I; and b) a suitable carrier.

The compounds of the present invention can be prepared according to following reaction scheme:

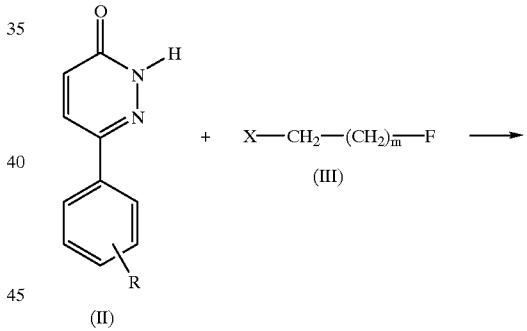

(II)

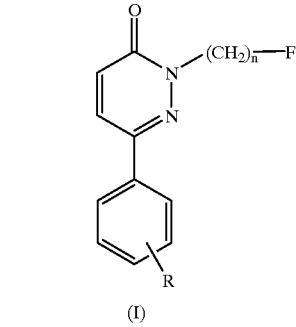

(I)

wherein R and n are as described above: m is 1, 3, 5, or 7; and X is halogen, preferably, bromine or iodine.

The 6-phenylpyridazinone of formula II and an equal molar amount of the fluoroalkyl halide of formula III, can be mixed together in an inert organic solvent, preferably dichloromethane, in the presence of 1.0 to 1.2 mole-equivalent of 2N aqueous metal hydroxide, preferably potassium hydroxide, and a catalytic amount of a phase transfer catalyst such as tetrabutylammonium bromide. The reaction can be conducted at room temperature overnight.

Phenylpyridazinones of formula II are known, see, e.g., *The Chemistry of Heterocyclic Compounds*, Vol. 28 (Interscience Publication, 1973). Fluoroalkyl halides of formula III are known and can be purchased commercially, e.g., from Oakwood Products Inc., West Columbia, S.C.

The present invention further relates to compositions comprising a) a pesticidally effective amount of a compound of formula I; and (b) a suitable carrier. Such suitable carriers may be solid or liquid in nature.

The compositions of the present invention can be prepared by formulating one or more pesticidal compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting insecticidal composition.

Alternatively, the pesticidal compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the pesticidal compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the pesticidal compound admixed therewith, can be dispersed in water to form a suspension for application in such form.

Granular formulations of the pesticidal compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The pesticidal compounds of this invention can be dissolved in a solvent and sprayed onto an inert mineral carrier such as attapulgite granules (10–100 mesh), and the solvent is then evaporated. Such granular compositions can contain from 2–25% of a compound of this invention, based on carrier plus compound, preferably, 3–15%. In addition, the pesticidal compounds of this invention can also be incorporated into a polymeric carrier such as polyethylene, polypropylene, butadiene-styrene, styrene-acryonitrile resins, polyamides, poly(vinyl acetates), and the like. When encapsulated, the pesticidal compounds of this invention can advantageously be released over an even longer time period, extending its effectiveness further than when used in non-encapsulated form.

Another method of applying the pesticidal compounds of this invention to the loci to be treated is by aerosol treatment, for which the pesticidal compound can be dissolved in an aerosol carrier which is a liquid under pressure but which is a gas at ordinary temperature (e.g., 20° C.) and atmospheric pressure. Aerosol formulations can also be prepared by first dissolving the pesticidal compound in a less volatile solvent and then admixing the resulting solution with a highly volatile liquid aerosol carrier.

For treatment of plants (such term including plant parts), the pesticidal compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The pesticidal compounds of this invention can be mixed with such surface-active dispersing agents, with or without an organic solvent, as concentrates for the subsequent addition of water, to yield aqueous suspensions of the pesticidal compounds at desired concentration levels.

In addition, the pesticidal compounds of this invention can be employed with carriers which themselves are pesticidally active, such as, e.g., insecticides, acaricides, fungicides, bactericides, and the like.

It will be understood that the effective amount of a pesticidal compound of this invention in a given formulation will vary depending, e.g., upon the specific chemical composition and formulation of the compound being employed, the method of applying the compound/formulation, the pest to be controlled, and the locus of treatment. Generally, however, the effective amount of the pesticidal compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat mites or insects, sprays of the active compounds can be applied to any suitable locus, such as to the mites or insects directly and/or to plants upon which they feed or nest. The pesticidal compositions of this invention can also be applied to the soil or other medium in which the mites or insects are present.

The specific methods of application of the pesticidal compounds and compositions of this invention, as well as the selection and concentration of these compounds, will vary depending upon such circumstances as crops to be protected, geographic area, climate, topography, plant tolerance, etc.

Compounds of this invention are useful as insecticides, acaricides, and/or nematicides, for foliar and/or soil application.

The following examples are provided to illustrate the present invention.

EXAMPLES

Example 1

Preparation of 2-(2-fluoroethyl)-6-(4-fluorophenyl)-3-(2H)-pyridazinone (Compound No. 3)

To a solution of 2 g (10.5 mmole) of 6-(4-fluoro-phenyl)-3-(2H)-pyridazinone in 100 ml of dichloromethane was added 0.5 g of tetrabutylammonium bromide, followed by an aqueous solution of KOH (0.71 g/10 ml), and the resultant reaction mixture was then stirred. After 20 minutes of stirring, a solution of fluoroethyl bromide (1.42 g, 11.5 mmole) in 10 ml dichloromethane was then added dropwise to the flask and the resultant reaction mixture was stirred overnight at room temperature.

The reaction mixture was then poured into water and extracted with dichloromethane. The organic layer was then washed with saturated aqueious sodium chloride, and dried over $MgSO_4$ and filtered. The filtrate was evaporated to produce a sticky white powder. The white powder was then triturated in hexane to produce 1.3 g of 2-(2-fluoroethyl)-6-(4-fluorophenyl)-3-(2H)-pyridazinone as a white solid, mp=145° C.

Compounds 1, 2, and 4–11 in Table 1 below were prepared using the same process as described in Example 1 except for a different starting phenylpyridazinone. Each of the compounds so formed is characterized in Table 1 by its NMR data and its melting point (MP).

TABLE 1

[Structure: pyridazinone with N-(CH₂)ₙ-F substituent and phenyl group with R substituent]

| No. | R | n | MP (° C.) | HNMR Data(TMS-δ=PPM) |
|-----|------|---|-----------|----------------------|
| 1 | H | 2 | (Oil) | (CDCl₃): 7.32–8.10(m, 6H), 7.06(d, 1H), 5.25(t, 1H), 4.72(t, 1H), 4.40(t+t, 2H) |
| 2 | H | 4 | (Oil) | (CDCl₃): 7.36–7.90(m, 6H), 6.98(d, 1H), 4.88(t, 1H), 4.30(t+t, 2H), 4.14(t, 1H), 1.84–2.15(m, 4H) |
| 3 | 4-F | 2 | 145 | (CDCl₃): 7.70–8.10(m, 3H), 6.90–7.32(m, 3H), 5.20(t, 1H), 4.66(t, 1H), 4.30(t+t, 2H) |
| 4 | 4-F | 4 | (Oil) | (CDCl₃): 7.70–7.98(m, 2H), 7.82(d, 1H), 7.05–7.30(m, 2H), 6.98(d, 1H), 4.90(t, 1H), 4.28(t+t, 2H), 4.15(t, 1H), 1.75–2.15(m, 4H) |
| 5 | 4-Cl | 2 | 126–129 | (DMSO-d₆): 7.42–8.12(m, 5H), 7.06(d, 1H), 5.22(t, 1H), 4.65(t, 1H), 4.30(t+t, 2H) |
| 6 | 4-Cl | 4 | (Oil) | (CDCl₃): 7.40–7.85(m, 5H), 7.00(d, 1H), 4.90(t, 1H), 4.30(t, 1H), 4.15(t+t, 2H), 1.65–2.15(m, 4H) |
| 7 | 3,4-Cl₂ | 2 | 133–134 | (CDCl₃): 7.66–7.90(m, 3H), 7.16(d, 1H), 7.00(d, 1H), 5.20(t, 1H), 4.78(t, 1H), 4.39 (t+t, 2H) |
| 8 | 3,4-Cl₂ | 4 | 53–54 | (CDCl₃): 7.56–7.90(m, 3H), 7.58(d, 1H), 7.00(d, 1H), 4.90(t, 1H), 4.30(t, 1H), 4.14(t+t, 2H), 1.58–2.18(m, 4H) |
| 9 | 4-I | 2 | (Oil) | (CDCl₃): 7.35–7.82(m, 5H), 6.98(d, 1H), 5.22(t, 1H), 4.74(t, 1H), 4.32(t+t, 2H) |
| 10 | 4-I | 4 | (Oil) | (CDCl₃): 7.32–7.84(m, 5H), 6.95(d, 1H), 4.84(t, 1H), 4.22(t, 1H), 4.10(t+t, 2H), 1.55–2.20(m, 4H) |
| 11 | 3-NO₃ | 2 | 175–180 | (DMSO-d₆): 7.75–8.55(m, 5H), 7.15(m, 1H), 5.25(t, 1H), 4.70(t, 1H), 4.36(t+t, 2H) |
| 12 | 3-CF₃ | 2 | 77–78 | (CDCl₃): 7.54–8.05(m, 5H), 7.06(d, 1H), 5.24(t, 1H), 4.76(t, 1H), 4.42(t+t, 2H) | m = multiple; d = doublet; t = triplet
δ = chemical shift in ppm relative to internal standard tetramethylsilane (TMS)

Example A

Stock Solution Preparation

The remaining examples relate to the pesticidal use of the compounds of this invention. In all these examples, a stock solution for the compounds was prepared at 3000 ppm by dissolving 0.24 gram of each compound to be tested in 8 ml of acetone and adding 72 ml of distilled water plus 3 drops of ethoxylated sorbitan monolaurate, a wetting agent. This stock solution was used in the remaining examples demonstrating the pesticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

Example B

Mite Adulticide and Mite Ovicide Tests

One day before treatment of cowpea primary leaves with the test solutions, a "FIG. 8" configuration of tree tanglefoot was applied to each of two cowpea primary leaves, one from each of two plants in a pot. In each figure, the circle nearer the stem was designated for the mite ovicide test and the circle further from the stem was designated for the mite adulticide test.

Groups of adult mites (*Tetranychus urticae* Koch) were transferred into ovicide circles one day before treatment and the females were allowed to deposit eggs until one hour before treatment, at which point all the adults were removed. The plants were then sprayed to run off with a 1000 ppm solution diluted from the 3000 ppm stock solution.

One day following treatment of the plants with the test solution, groups of approximately 25 adult mites were transferred into the adulticide rings. Five days later these rings were examined for live mites remaining on the leaves. The percent control was estimated based on the number of mites surviving on the control plants.

Nine days following treatment the ovicide rings were examined for unhatched eggs and living immature mites. The percent control was estimated based on the number of unhatched eggs.

Results of the mite adulticide (MI) and ovicide (MIOV) tests are presented below in Table 2.

Example C

Rice Planthopper Foliar Test

The stock solution of 3000 ppm prepared in Example A above, was diluted to 1000 ppm. One pot containing approximately 20 Mars variety rice seedlings was treated with each formulation by spraying with a spray atomizer. One day after treatment plants were covered with a tubular cage and twenty adult rice delphacids, *Sogatodes orizicola*, were transferred into each cage. Five days after transferring, counts were made of the surviving planthoppers in each pot and percent control was estimated.

Results of the testing of rice planthoppers (RPH) are presented in Table 2 below.

Example D

Tobacco Budworm Test

For each compound tested, 0.2 ml of the stock solution prepared in Example A above, was pipetted onto the surface of each of 5 diet cells, allowed to spread over the surfaces and air dried for two hours. Then a second instar *Helicoverpa virescens* larva was introduced into each cell. After 14 days, the number of living larvae was determined for each treatment and percent control, corrected by Abbott's formula, was calculated.

The results of the testing of tobacco budworms (TB) are presented in Table 2 below.

Example E

Southern Corn Rootworm Test

The stock solution of 3000 ppm was diluted to 100 ppm (test solution). For each compound, 2.5 ml of the test solution was pipetted onto a filter paper (Whatman #3) at the bottom of a 100 mm petri dish. Two corn seedlings were soaked in the 100 ppm solution for 1 hour and transferred to the petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18: 265–267 (1925)] was calculated.

The results of the testing of Southern Corn Rootworm (CR) are presented below in Table 2.

Example F

Nematode Test

The stock solution (3000 ppm) was diluted to 1000 ppm (test solution). For each test solution, 25 ml was drenched onto separate 500 grams of soil infested with root knot nematode (*Meloidogyne incognita*) eggs in a pot, for a soil concentration of 50 ppm sc.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table 2 below.

TABLE 2

| | Pesticidal Activity | | | | | |
|---|---|---|---|---|---|---|
| Cmpd. | | | Percent Control | | | |
| No. | MI | MIOV | RPH | TB | CR | NE |
| 1 | 0 | 100 | 0 | 0 | 0 | 0 |
| 2 | 0 | 100 | 0 | 0 | 0 | 0 |
| 3 | 0 | 100 | 0 | 50 | 0 | 0 |
| 4 | 0 | 100 | 0 | 0 | 0 | 0 |
| 5 | 0 | 100 | 0 | 0 | 0 | 0 |
| 6 | 0 | 100 | 0 | 0 | 0 | 0 |
| 7 | 0 | 100 | 0 | 100 | 0 | 0 |
| 8 | 0 | 0 | 0 | 0 | 0 | 100 |
| 9 | 0 | 0 | 100 | 0 | 0 | 0 |
| 10 | 0 | 70 | 0 | 0 | 0 | 0 |
| 11 | 98 | 0 | 0 | 0 | 0 | 0 |
| 12 | 95 | 100 | 0 | 0 | 100 | 100 |

What is claimed is:

1. A miticidal, insecticidal, or nematicidal phenylpyridazinone compound of the formula

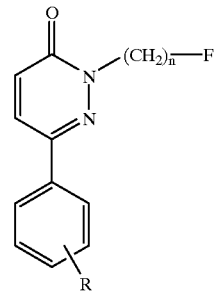

(I)

wherein n is 2, 4, 6, or 8, and R is one or more groups selected from halogen, nitro, $C_1$–$C_4$ haloalkyl, amino, carboxyl, and cyano.

2. A compound as recited in claim 1 wherein R is one or more groups selected from halogen and $C_1$–$C_4$ haloalkyl.

3. A compound as recited in claim 2 wherein R is one or two groups selected from halogen and trihalomethyl.

4. A compound as recited in claim 3 wherein R is one or two halogen.

5. A compound as recited in claim 2 wherein R is one or two trihalomethyl.

6. A compound as recited in claim 1 wherein n is 2 or 4.

7. A compound as recited in claim 6 wherein n is 2.

8. A miticidal insecticidal, or nematicidal composition comprising: a) an effective amount of a miticidal, insecticidal, or nematicidal compound as recited in claim 1; and b) a suitable carrier.

9. A method for controlling acarids which comprises applying an effective amount of a acaricidal compound as recited in claim 1 to the locus to be protected.

10. A method for controlling insects which comprises applying an effective amount of an insecticidal compound as recited in claim 1 to the locus to be protected.

11. A method for controlling nematodes which comprises applying an effective amount of a nematicidal compound as recited in claim 1 to the locus to be protected.

* * * * *